United States Patent
Finlay et al.

(10) Patent No.: US 9,593,363 B2
(45) Date of Patent: Mar. 14, 2017

(54) METHODS AND MODELS FOR ASSESSING ANTI-AGING BENEFITS OF AGENTS

(71) Applicant: The Procter & Gamble Company, Cincinnati, OH (US)

(72) Inventors: Deborah Ruth Finlay, Cincinnati, OH (US); Rosemarie Osborne, Oxford, OH (US); Charles Carson Bascom, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/919,325

(22) Filed: Jun. 17, 2013

(65) Prior Publication Data

US 2013/0337087 A1 Dec. 19, 2013

Related U.S. Application Data

(60) Provisional application No. 61/661,175, filed on Jun. 18, 2012.

(51) Int. Cl.
*C12Q 1/68* (2006.01)
*A61P 17/00* (2006.01)

(52) U.S. Cl.
CPC ............. *C12Q 1/68* (2013.01); *C12Q 1/6883* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 3,755,560 | A | 8/1973 | Dickert et al. |
| 4,421,769 | A | 12/1983 | Dixon |
| D391,162 | S | 2/1998 | Kokenge |
| D516,436 | S | 3/2006 | Campbell |
| D535,191 | S | 1/2007 | Corker |
| D542,660 | S | 5/2007 | Thomas |
| D547,193 | S | 7/2007 | Blasko |
| D547,661 | S | 7/2007 | Blasko |
| D558,591 | S | 1/2008 | Blasko |
| D563,221 | S | 3/2008 | Ashiwa |
| D570,707 | S | 6/2008 | Blasko |
| 7,654,420 | B2 | 2/2010 | Honda |
| 8,324,447 | B2 | 12/2012 | Goldstein |
| 2007/0040306 | A1 | 2/2007 | Morel |
| 2008/0206770 | A1* | 8/2008 | Zobel et al. ............... 435/6 |
| 2009/0017080 | A1 | 1/2009 | Tanner |
| 2009/0110709 | A1 | 4/2009 | Mitts |
| 2009/0298113 | A1 | 12/2009 | Vielhaber |
| 2011/0262570 | A1* | 10/2011 | Finlay et al. ............... 424/745 |
| 2012/0034613 | A1 | 2/2012 | Gopaul et al. |
| 2012/0271219 | A1* | 10/2012 | Weisgerber et al. ........ 604/20 |

FOREIGN PATENT DOCUMENTS

| | | |
|---|---|---|
| EP | 2019316 | 1/2009 |
| WO | WO2006/036943 | 4/2006 |
| WO | WO2010/118419 | 10/2010 |
| WO | WO2011/097572 | 8/2011 |

OTHER PUBLICATIONS

Szauter et al., "A novel fibrotic disorder associated with increased dermal fibroblast proliferation and downregulation of genes of the microfibrillar network" 163 British Journal of Dermatology 1102-1115 (2010).*
Langton et al., "Differential expression of elastic fibre components in intrinsically aged skin" 13 Biogerontology 37-48 (Apr. 2, 2011).*
Steinstraesser et al., "A Human Full-Skin Culture System for Interventional Studies" 9 Eplasty e5 27-40 (2009).*
"Genomics of Skin Aging: Practical Applications", Journal of Drugs in Dermatology Supplement, vol. 8, Issue 7 (2009).
Bissett el al. "Niacinamide: A B Vitamin that Improves Aging Facial Skin Appearance" American Society for Dermatologic Surgery Inc., Dermatol Surg 2005; 31:860-865.
Draelos "Clinical Situations Conducive to Proactive Skin Health and Anti-Aging Improvement", The Society for Investigative Dermatology 2008, pp. 25-27.
In Vitro Biomarker Responses to a New Anti-Aging Peptide, PAL-KT, Osborne et al, American Academy of Dermatology 67th Annual Meeting Media Resources, 2009.
Skin Biomarkers Confirm the Anti-Oxidant Activity of Olive Derivatives and Yeast Ferment Filtrate, Finlay et al., P&G 67th Annual Meeting of American Academy of Dermatology (2009).
Osborne, R. et al. "Application of Genomics to Breakthroughs in the Cosmetic Treament of Skin Ageing and Discoloration" British Journal of Dermatology 2012 166 (Suppl. 2), pp. 16-19.
International Search Report PCT/US2013/046089; Mailing Date Sep. 9, 2013; 14 pages.

* cited by examiner

*Primary Examiner* — Nancy J Leith
(74) *Attorney, Agent, or Firm* — John G. Powell

(57) ABSTRACT

A screening method for identifying an agent as effective for providing an anti-aging skin benefit is provided. The screening method includes culturing first and second human skin samples from about 3 days to about 19 days, wherein the first and second human skin samples are derived from a human skin surgical waste tissue. The first human skin sample is contacted with at least one test agent. The second human skin sample is contacted with a positive control. Transcriptional profiles are generated from the first and second human skin samples, and the at least one test agent is identified as effective for providing an anti-aging skin benefit when the transcriptional profiles of at least two genes show a similar directional change in comparison to one or more untreated control tissue samples.

11 Claims, 15 Drawing Sheets

| Gene | Gene |
|---|---|
| DERMAL PANEL | BASEMENT MEMBRANE/ LIPID PANEL |
| FBN1 | |
| FBLN1 | |
| TNXB | COL4A1 |
| FN1 | LAMA5 |
| LOXL2 | |
| COL3A1 | EPIDERMAL PANEL |
| COL1A1 | KRT2 |
| ELN | KRT6A |
| LOXL1 | CLDN1 |
| | LOR |
| GROWTH FACTOR/HA/ SENESCENCE PANEL | FLG |
| | IVL |
| | KRT10 |
| | AQP3 |
| TGFB2 | KRT14 |
| TGFBR3 | |
| TGFB3 | |
| TGFB1 | |
| TGFBR2 | |
| TGFBR1 | |
| CTGF | |
| | |
| RETINOID METABOLISM PANEL | |
| CYP26A1 | |
| CYP26B1 | |
| ALDH1A2 | |
| RDH10 | |
| RARRES1 | |
| LRAT | |
| CRABP2 | |
| RARG | |
| CEBPA | |

Fig. 3

| Up-Down Regulation (comparing to control group) Day 4 and Day 7 | | | | | | | | | | |
|---|---|---|---|---|---|---|---|---|---|---|
| Tissue DAY 4 | TGFβ-1 20ng/ml | Niacinamide 0.2% | Olive Oil Extract 0.0005% | peptide15ppm | | Tissue DAY 7 | TGFβ-1 20ng/ml | Niacinamide 0.2% | Olive Oil Extract 0.0005% | peptide15ppm |
| FBN1 | -1.27 | -1.04 | -1.14 | -2.79 | | FBN1 | 5.45 | 1.64 | 2.80 | 2.47 |
| FBLN1 | -1.13 | 1.00 | -1.31 | -1.79 | | FBLN1 | 2.69 | 1.76 | 2.28 | 2.10 |
| TNXB | 1.13 | 1.07 | 1.02 | 1.19 | | TNXB | 1.07 | -1.08 | 1.38 | 1.82 |
| FN1 | 2.10 | -1.45 | 1.22 | 1.36 | | FN1 | 1.80 | -1.31 | 1.10 | -1.44 |
| LOXL2 | 1.02 | -1.08 | 1.05 | 1.20 | | LOXL2 | 1.18 | 2.08 | 1.83 | 1.50 |
| COL3A1 | 1.42 | -1.03 | -1.09 | 1.08 | | COL3A1 | -1.01 | 1.18 | 1.81 | 1.16 |
| COL1A1 | 1.71 | 1.02 | -2.08 | -1.74 | | COL1A1 | 1.62 | 1.40 | 4.08 | 2.31 |
| ELN | 1.09 | 1.13 | -1.12 | 1.53 | | ELN | 1.02 | 1.08 | 3.76 | 3.48 |
| LOXL1 | 1.10 | 1.90 | 1.08 | -1.06 | | LOXL1 | 1.65 | 2.83 | 2.57 | 3.13 |
| TGFB2 | 4.69 | 1.66 | 1.12 | 2.11 | | TGFB2 | 1.76 | -1.19 | 2.25 | 2.66 |
| TGFBR3 | 2.74 | -1.02 | 1.08 | 1.68 | | TGFBR3 | 1.15 | -1.33 | 1.62 | 1.83 |
| TGFB3 | 1.68 | -1.30 | -1.48 | 1.32 | | TGFB3 | 1.17 | 1.15 | 1.64 | 2.58 |
| TGFB1 | 1.22 | 1.01 | 1.10 | 1.47 | | TGFB1 | -1.59 | -1.73 | -1.21 | 1.20 |
| TGFBR2 | -1.01 | -1.42 | -1.31 | -1.34 | | TGFBR2 | -1.63 | 1.34 | -1.29 | -1.23 |
| TGFBR1 | -1.47 | 2.73 | -1.06 | -1.13 | | TGFBR1 | -1.05 | 1.49 | -1.35 | -1.34 |
| CTGF | 1.04 | 2.72 | -1.83 | -1.56 | | CTGF | -1.10 | 2.09 | 1.34 | 1.53 |
| COL4A1 | 1.04 | -1.03 | -1.34 | -1.27 | | COL4A1 | 1.65 | 1.60 | 1.67 | 1.51 |
| LAMA5 | -1.06 | -1.89 | -1.51 | -1.54 | | LAMA5 | 2.43 | 1.64 | 1.78 | 1.55 |

| Up reg | $p \leq 0.05$ | Down reg | $p \leq 0.05$ |
|---|---|---|---|
| Up reg | $p \leq 0.10$ | Down reg | $p \leq 0.10$ |

Fig. 4

| Gene Name | | p-value (comparing to untreated control group) | | | | |
|---|---|---|---|---|---|---|
| | | tRA 0.0025% Media | tRA 0.00125% Media | Retinol 0.1% Topical | Retinol 0.2% Topical | RP 0.3% Topical |
| Keratin 2 | KRT2 | 0.000000 | 0.000010 | 0.002466 | 0.027170 | 0.157941 |
| Keratin 6A | KRT6A | 0.001150 | 0.001908 | 0.017714 | 0.096194 | 0.354905 |
| Claudin 1 | CLDN1 | 0.000000 | 0.000001 | 0.002001 | 0.026361 | 0.824871 |
| Loricrin | LOR | 0.000016 | 0.000838 | 0.000940 | 0.013881 | 0.063449 |
| Filaggrin | FLG | 0.000000 | 0.000085 | 0.004222 | 0.038162 | 0.266013 |
| involucrin | IVL | 0.006126 | 0.015421 | 0.004163 | 0.265140 | 0.712724 |
| Keratin 10 | KRT10 | 0.000000 | 0.000000 | 0.000001 | 0.000148 | 0.021678 |
| Aquaporin 3 | AQP3 | 0.210998 | 0.000253 | 0.000008 | 0.000173 | 0.044209 |
| Keratin 14 | KRT14 | 0.000000 | 0.000000 | 0.183800 | 0.000001 | 0.000159 |

| 48hr | 0.0006% tRA | 0.3% Retinyl proprionate |
|---|---|---|
| CYP26A1 | 1.41 | -1.25 |
| CYP26B1 | 3.09 | 1.16 |
| ALDH1A2 | 1.07 | -1.02 |
| RDH10 | -1.00 | -1.01 |
| RARRES1 | 2.27 | 1.39 |
| LRAT | 1.04 | 1.26 |
| CRABP2 | 2.32 | 1.03 |
| RARG | 1.44 | 1.33 |
| CEBPA | 1.43 | 1.53 |

Fig. 6A

| 5 days | 0.0006% tRA | 0.3% Retinyl proprionate |
|---|---|---|
| CYP26A1 | -1.00 | 1.13 |
| CYP26B1 | 2.40 | 1.22 |
| ALDH1A2 | 1.13 | 1.37 |
| RDH10 | -1.24 | -1.17 |
| RARRES1 | 1.57 | 5.71 |
| LRAT | -1.37 | -1.17 |
| CRABP2 | 4.78 | 1.31 |
| RARG | 1.26 | -1.01 |
| CEBPA | -1.26 | -1.11 |

Fig. 6B

| 7 day | 0.0006% tRA | 0.3% Retinyl proprionate |
|---|---|---|
| CYP26A1 | -1.65 | -2.52 |
| CYP26B1 | 4.67 | 1.71 |
| ALDH1A2 | -3.24 | -4.15 |
| RDH10 | -2.35 | -3.08 |
| RARRES1 | -1.64 | -3.70 |
| LRAT | -2.55 | -3.75 |
| CRABP2 | 4.13 | 2.34 |
| RARG | 2.12 | 1.67 |
| CEBPA | 1.32 | 1.98 |

Fig. 6C

Day 5

|       | TGFβ1 20ng/ml -5d | Niacinamide 0.25% -5d |
|-------|-------------------|----------------------|
| FBN1  | 1.06              | 1.32                 |
| FBLN1 | -1.77             | 2.26                 |
| TNXB  | 1.09              | 1.58                 |
| FN1   | 3.33              | 1.12                 |
| LOXL2 | 1.08              | 1.54                 |
| COL3A1| 1.96              | 1.18                 |
| COL1A1| 3.06              | 1.15                 |
| ELN   | 1.52              | 1.87                 |
| LOXL1 | 1.43              | 1.26                 |

Day 7

|       | TGFβ1 20ng/ml -7d | Niacinamide 0.25% -7d |
|-------|-------------------|----------------------|
| FBN1  | 1.40              | 1.66                 |
| FBLN1 | -1.24             | 2.78                 |
| TNXB  | -1.10             | 1.30                 |
| FN1   | 5.02              | 1.59                 |
| LOXL2 | 1.35              | 1.40                 |
| COL3A1| 2.87              | 1.59                 |
| COL1A1| 6.48              | 1.67                 |
| ELN   | 1.75              | 1.46                 |
| LOXL1 | 1.35              | -1.16                |

Fig. 7A      Fig. 7B

| timecourse | | | | |
|---|---|---|---|---|
| Single donor 10/26/10 | TGFβ1 20ng/ml 24hr | TGFβ1 20ng/ml 48 hrs | TGFβ1 20ng/ml day5 | TGFβ1 20ng/ml day7 |
| FBN1 | 1.15 | -1.09 | 1.06 | 1.40 |
| FBLN1 | -1.05 | -1.09 | 1.54 | -1.25 |
| TNXB | -1.01 | -1.16 | 1.09 | -1.10 |
| FN1 | 1.84 | 1.71 | 3.33 | 5.02 |
| LOXL2 | 1.35 | 1.10 | 1.08 | 1.35 |
| COL3A1 | 1.50 | 1.53 | 1.96 | 2.87 |
| COL1A1 | 1.07 | 1.75 | 3.06 | 6.48 |
| ELN | 1.83 | 1.09 | 1.52 | 1.75 |
| LOXL1 | -1.33 | -1.01 | 1.43 | 1.35 |

|  | 37 degrees | | | | |
|---|---|---|---|---|---|
|  | Donor #1 | Donor #2 | Donor #3 | Donor #4 | Donor #5 |
| FBN1 | 1.40 | 1.20 | 1.14 | 2.05 | 4.42 |
| FBLN1 | -1.25 | -1.27 | -1.31 | -1.20 | 2.22 |
| TNXB | -1.10 | -1.09 | -1.12 | -1.10 | 4.74 |
| FN1 | 5.02 | 5.12 | 4.48 | 7.48 | -1.74 |
| LOXL2 | 1.35 | 1.32 | 1.48 | 3.26 | 1.34 |
| COL3A1 | 2.87 | 2.67 | 3.60 | 7.83 | 8.26 |
| COL1A1 | 6.48 | 4.64 | 4.77 | 9.90 | 1.45 |
| ELN | 1.75 | 2.60 | 3.20 | 5.74 | 1.44 |
| LOXL1 | 1.35 | 1.31 | 1.39 | 2.43 | -1.64 |

Fig. 9A

|  | 33 degrees | | | | |
|---|---|---|---|---|---|
|  | Donor #6 | #7 | Donor #8 | Donor #9 | Donor #10 |
| FBN1 | 1.43 | -1.04 | 1.44 | 2.29 | -1.25 |
| FBLN1 | 1.22 | 1.28 | -1.05 | 2.34 | -1.15 |
| TNXB | 1.59 | -1.25 | -1.70 | 1.49 | 1.01 |
| FN1 | 3.43 | 5.42 | 6.44 | 2.06 | 2.13 |
| LOXL2 | 1.54 | 1.15 | -1.42 | 1.11 | -1.04 |
| COL3A1 | 1.67 | 1.77 | 4.57 | 1.30 | 1.77 |
| COL1A1 | 4.98 | 1.83 | 1.17 | 1.64 | 2.52 |
| ELN | 1.27 | 1.14 | -2.87 | -1.00 | 1.40 |
| LOXL1 | 1.24 | 1.29 | 1.57 | 1.02 | 1.18 |

Fig. 9B

|  | Niacinamide 0.2% 33C | Olive Oil Extract 33C |  | Niacinamide 0.2% 37C | Olive Oil Extract 37C |
|---|---|---|---|---|---|
| *FBN1* | 1.08 | -1.53 | *FBN1* | 1.23 | 1.19 |
| *FBLN1* | 1.59 | -1.31 | *FBLN1* | 1.53 | 1.42 |
| *TNXB* | 1.11 | -1.04 | *TNXB* | 1.28 | 1.53 |
| *FN1* | -1.16 | -1.09 | *FN1* | 1.17 | 1.33 |
| *LOXL2* | -1.03 | -1.53 | *LOXL2* | 1.19 | 1.55 |
| *COL3A1* | 1.16 | -1.56 | *COL3A1* | 1.15 | 1.02 |
| *COL1A1* | 1.65 | -1.04 | *COL1A1* | 1.57 | -1.04 |
| *ELN* | 1.16 | -1.10 | *ELN* | 1.49 | 1.36 |
| *LOXL1* | 1.17 | -1.33 | *LOXL1* | 1.15 | 1.30 |

Fig. 10

ARRIVAL  DAY 1  DAY 4  DAY 6  DAY 8  DAY 11

DAY 1  DAY 2  DAY 3  DAY 4  DAY 6  DAY 10

24 HRS  DAY 6  DAY 9  DAY 12  DAY 14  DAY 17  DAY 19

DAY 1  DAY 3  DAY 5  DAY 7  DAY 9  DAY 11

| TGFB summary | Donor 1 | Donor 2 | Donor 3 | Donor 4 | Donor 5 | Donor 6 | Donor 7 | Donor 8 | Donor 9 | Donor 10 |
|---|---|---|---|---|---|---|---|---|---|---|
| FBN1 | 1.72 | 1.51 | 1.06 | -1.05 | 1.18 | -1.21 | 1.43 | -1.23 | 2.58 | 1.10 |
| FBLN1 | -1.28 | -1.36 | -1.47 | -2.33 | -2.05 | -2.09 | 1.23 | -2.01 | -1.01 | -1.19 |
| TNXB | -1.27 | -1.2 | -1.54 | -1.96 | -1.74 | -2.12 | 1.45 | -1.83 | 1.07 | -1.23 |
| FN1 | 9.66 | 5.73 | 3.27 | 3.52 | 7.27 | 2.79 | 4.82 | 3.09 | 13.33 | 4.57 |
| LOXL2 | 1.5 | 1.37 | 1.17 | -1.23 | 1.32 | -1.26 | 2.45 | 1.23 | 2.18 | -1.01 |
| COL3A1 | 5.67 | 3.76 | 2.65 | 5.03 | 2.09 | 1.21 | 2.82 | 2.74 | 12.70 | 3.12 |
| COL1A1 | 5.73 | 6.27 | 3.12 | 5.14 | 4.09 | 1.01 | 4.86 | 2.1 | 7.92 | 3.33 |
| ELN | 2.68 | 1.92 | 1.86 | 1.97 | 4.59 | -1.2 | 4.26 | 1.87 | 6.01 | 3.79 |
| LOXL1 | 1.11 | 1.66 | 1.1 | 1.06 | 1.34 | -1.49 | 1.86 | 1.44 | 2.64 | 1.28 |

| | |
|---|---|
| Up reg | p ≤ 0.05 |
| Up reg | p ≤ 0.10 |
| Down reg | p ≤ 0.05 |
| Down reg | p ≤ 0.10 |

Fig. 15

|  | TGFB1 (20ng/ml) | Test Compound 0.5% | Test Compound 0.1% |
|---|---|---|---|
| *FBN1* | -1.00 | 1.51 | -2.75 |
| *FBLN1* | -1.21 | 1.89 | 1.38 |
| *TNXB* | -3.51 | 1.32 | 1.23 |
| *FN1* | 3.86 | 1.13 | -1.13 |
| *LOXL2* | 1.23 | 1.55 | 1.28 |
| *COL3A1* | 2.31 | 1.49 | 1.27 |
| *COL1A1* | 4.17 | 1.60 | 1.26 |
| *ELN* | 2.04 | 3.11 | 2.04 |
| *LOXL1* | 1.26 | 1.64 | 1.50 |

Fig. 16

| Gene | Artichoke Leaf Extract 0.03% [A] | Carob Fruit Extract 0.005% [B] | Blend of Artichoke Leaf Extract 0.03% + Carob Fruit Extract 0.005% [C] | Expected Additive Effect of Combination [Sum of A + B] |
|---|---|---|---|---|
| *KRT2 | 1.50 | -1.35 | 1.72* | 0.15 |
| KRT6A | -1.05 | -1.34 | 1.26 | -2.39 |
| CLDN1 | -1.03 | -1.3 | 1.07 | -2.33 |
| LOR | 1.49 | -1.07 | 1.33 | 0.42 |
| *FLG | 1.58 | -1.26 | 1.76* | 0.32 |
| IVL | -1.06 | -1.68 | 1.06 | -2.74 |
| KRT10 | -1.1 | -1.78 | 1.79 | -2.88 |
| AQP3 | 1.04 | -1.46 | 1.26 | -0.42 |
| *KRT14 | 1.11 | -1.13 | 1.34* | -0.02 |

\* Statistically significant p < 0.1

\*\* Statistically significant p < 0.05

Fig. 17

|  | Olive Oil Extract 0.001% | Artichoke Leaf Extract 0.03% | Combination of Olive Oil Extract and Artichoke Leaf Extract |
|---|---|---|---|
| FBN1 | -2.08 | -3.03 | 2.42 |
| FBLN1 | -1.32 | -2.02 | 2.73 |
| TNXB | -1.51 | -2.07 | 2.48 |
| FN1 | -2.15 | -2.11 | 1.75 |
| LOXL2 | -2.08 | -2.41 | 1.78 |
| COL3A1 | -2.31 | -2.86 | 1.66 |
| COL1A1 | -1.92 | -2.47 | -1.44 |
| ELN | -1.11 | -1.74 | 4.29 |
| LOXL1 | 1.25 | -1.07 | 2.22 |

Fig. 18

METHODS AND MODELS FOR ASSESSING ANTI-AGING BENEFITS OF AGENTS

FIELD

One aspect of the invention relates to novel ex-vivo skin models and screening methods for identifying anti-aging agents that may be suitable for use in cosmetic compositions.

BACKGROUND

Skin is a complex, multi-layered and dynamic system that is the largest organ of the body and is vitally important to both our health and self image. Skin, which comprises three principal layers (e.g., the epidermis, the dermis, and the hypodermis or subcutis layer), contains a wide variety of cellular types and structures, including epidermal and dermal connective tissue with blood and lymphatic vessels, hypodermal adipose tissue, and the elastic fascia beneath the hypodermis. In turn, these structures are composed of a number of different cellular types including keratinocytes, melanocytes, fibroblasts, endothelial cells, and adipocytes.

Skin aging is a complex, multi-factorial process that can result from unrepaired cellular and tissue damage, which can be caused by a variety of intrinsic and extrinsic factors occurring over decades. Some of the biological themes/pathways believed to be involved with aging skin include lipid biosynthesis, epidermal cell differentiation, extracellular matrix organization and biogenesis, wound healing, immune response, and inflammatory response. See, e.g., Genomics of Skin Aging: Practical Applications, Journal of Drugs in Dermatology Supplement, Vol. 8, Issue 7 (2009). Over time, skin aging can result in, for example, the appearance of fine lines and wrinkles (an example of which is crow's feet in the periorbital area), damage to skin barrier properties resulting in skin dryness, skin sagging, a reduction in skin strength and elasticity, and so forth.

Given the significant impact that skin aging can have on one's appearance and self esteem, there is an on-going desire to identify cosmetic agents that are effective at treating or improving the appearance of aging skin. Skin models capable of mimicking aspects of cellular processes integral to skin aging are therefore desired in order, for example, to identify these agents. Modeling techniques to study skin physiology and skin responses to agents have historically included a variety of specific techniques, from the culturing of a single cell type or a small number of co-mingled cell types, to fabricating human tissue equivalents, to developing animal models. However these relatively simple models often lack much of the intra and intercellular complexities of human skin. For example, cell cultures of single cell types are easily utilized but overly simplistic and can have limitations for generalizing results to human skin First, such cultures contain cells that are altered simply by being cultured and, in some cases, have been altered by genetic manipulation to promote easy cell passaging and maintenance. Second, such cultures may not account for intrinsic intricate matrices of cells constantly interacting as a unit. Multi-celled cultures can be limited due to difficulties in creating the integrated mechanical structure of native tissue and in ensuring that the cells comprise the extracellular components necessary to maintain cellular genetic expression levels at a normal physiological level. Models that include stem cells treated to mimic human skin are suitable for their intended purposes, but can also fall victim to similar concerns and limitations.

More complex skin models include animal models and skin-equivalent models. While having additional complexity, animal models can suffer from limitations including the genetic variation with respect to human skin; in the analysis of obtained results there can be a concern that human tissues react differently from animal tissues and the ability to generalize results may be compromised.

Skin-equivalent models can be limited by lack of cellular interconnectivity, permeability concerns, and anatomical simplicity. Some recent attempts at skin-equivalent models may be described as organotypic human tissue equivalents and include in vitro reconstructions of human cells such as keratinocytes cultured on an inert polycarbonate filter. These models by their very nature may be limited in that they can have reduced barrier function that can lead to aberrant sensitivities to tested agents. The models may also be less complex than human skin, having perhaps one or two cells types (such as keratinocytes and fibroblasts or keratinocytes and melanocytes) but lacking additional cells such as endothelial cells or even the full keratinocyte, fibroblast, and melanocyte combination. In addition the organotypic skin equivalent models may also be missing normal skin structures such as glands that may affect skin response.

The most complex skin model involves the ex vivo culture of human skin tissue samples. Some previous attempts at such models included small biopsies of skin floating directly in media. It is known in the art that transient cultures may be deficient, as inventors and researchers have indicated attempts at ex-vivo pig skin grafts are limited to seven days (Vielhaber et al., Ex vivo Human Skin Model, US2009/0298113). Attempts at improving the longevity of ex-vivo skin have been sought, one example being described in EP 2 019 316 B1.

Even more recent ex-vivo models have involved attempting to culture skin explants on metal grids (Mitts et al., Elastin Protective Polyphenolics and Methods of Using the Same, US2009/0110709) and skin grafting to the chorioallantoic membrane (CAM) of a fertilized ovarian egg (Goldstein et al., Chimeric Avian-Based Screening System Containing Mammalian Grafts, US2009/0064349). However such models may be still limited by transiency of the construct, delicacy, and even xenogeneic concerns.

Despite these advancements, a need continues to exist for a sensitive and predictive ex-vivo human skin tissue screening methods and models suitable for screening tens or hundreds of compounds for select activity in a large number of tissue donors. However, there are many challenges/uncertainties associated with development of ex-vivo tissue culture models and methods that are predictable and repeatable for large numbers of test compounds across a large tissue donor population. Some non-limiting examples include one or more of: the effect of donor to donor variability, whether ex-vivo skin tissue can be properly regulated over the requisite culturing time periods, whether analysis of gene transcriptomics, proteomics, and/or metabomics of ex-vivo skin tissue can be predictive of in vivo results, whether appropriate positive controls could be identified for use in a high enough percentage of ex-vivo tissue samples to develop a satisfactory screening method, whether culturing conditions could be identified that enabled a sufficiently robust tissue response in a high enough percentage of ex-vivo tissue samples, and whether these variables could be controlled to the point that the effects of a test agent on an ex-vivo skin tissue sample could be isolated and interpreted.

SUMMARY

In one aspect of the invention, a screening method for identifying an agent as effective for providing an anti-aging skin benefit is provided. The screening method comprises culturing first and second human skin samples from about 3 days to about 19 days, wherein the first and second human skin samples are derived from a human skin surgical waste tissue. The first human skin sample is contacted with at least one test agent. The second human skin sample is contacted with a positive control. Transcriptional profiles are generated from the first and second human skin samples, and the at least one test agent is identified as effective for providing an anti-aging skin benefit when the transcriptional profiles of at least two genes show a similar directional change in comparison to one or more untreated control tissue samples.

BRIEF DESCRIPTION OF THE FIGURES

FIG. 3 is a table setting forth a non-limiting list of some genes suitable for inclusion in the models and methods described herein.

FIG. 4 is a heat map illustrating fold changes in ex vivo skin tissue samples for some of the genes listed in FIG. 3 over a time course of 4 days and 7 days;

FIG. 6A is a heat map illustrating fold changes in ex vivo skin tissue samples from treatment with tRA and retinol propionate over a time course of 48 hours;

FIG. 6B is a heat map illustrating fold changes in ex vivo skin tissue samples from treatment with tRA and retinol propionate over a time course of 5 days;

FIG. 6C is a heat map illustrating fold changes in ex vivo skin tissue samples from treatment with tRA and retinol propionate over a time course of 7 days;

FIG. 7A is a heat map illustrating fold changes in samples of ex vivo skin tissue following treatment with niacinamide over a 5 day time course;

FIG. 7B is a heat map illustrating fold changes in samples of ex vivo skin tissue following treatment with niacinamide over a 7 day time course;

FIG. 9A is a heat map illustrating fold changes in ex vivo skin tissue samples from multiple donors at 37 C;

FIG. 9B is a heat map illustrating fold changes in ex vivo skin tissue samples from multiple donors at 33 C;

FIG. 10 is a heat map illustrating fold changes in ex vivo skin tissue samples from treatment with several materials at culturing temperatures of 33 C and 37 C;

FIG. 15 is a heat map illustrating fold changes in ex vivo skin tissue samples from multiple donors from treatment with TGFβ-1;

FIG. 16 is a heat map illustrating fold changes in ex vivo skin tissue samples from treatment with a positive control and a test compound;

FIG. 17 is a table illustrating fold changes in ex vivo skin tissue samples from treatment with an artichoke leaf extract, a carob fruit extract, and a combination thereof; and FIG. 18 is a heat map illustrating fold changes in ex vivo skin tissue samples from treatment with an olive oil extract, an artichoke leaf extract, and a combination thereof.

DETAILED DESCRIPTION

Figure 1:
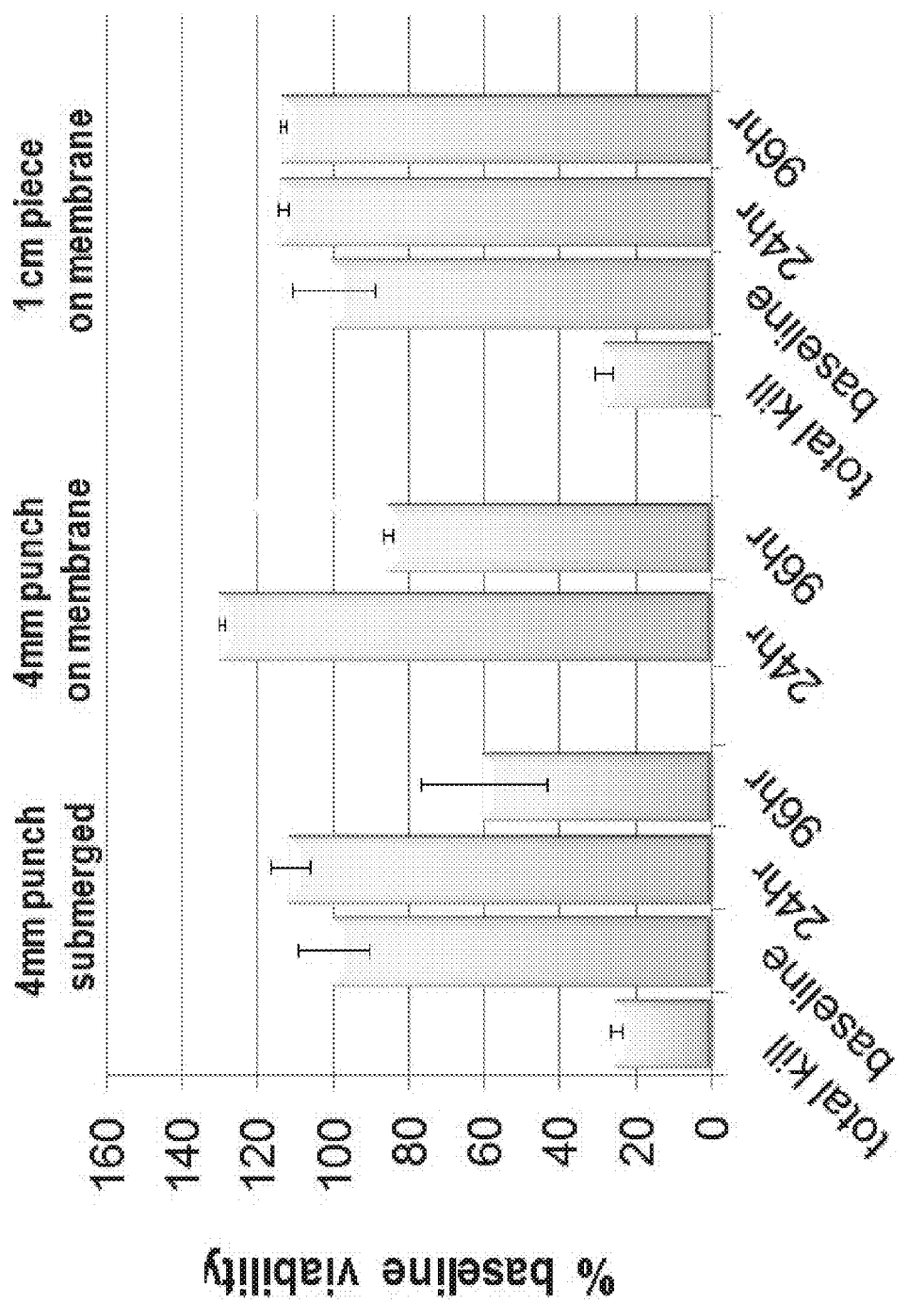
FIG. 1 is a bar graph illustrating the viability of ex-vivo skin tissue, as assessed in an MTT as say (3-(4,5-Dimethylthiazol-2-yl)-2,5-diphenyltetrazolium bromide assay).

Disclosed herein is an ex-vivo human skin model and screening methods that can be used to overcome the challenges and uncertainties of current technology. It is to be understood that the terminology used herein is for the purpose of describing particular embodiments only and is not intended to be limiting. As used in the description of the invention and appended claims, the singular "a," "an," and "the" are intended to include the plural forms as well, unless the context clearly indicates otherwise. The disclosure of any ranges in the specification and claims are to be understood as including the range itself and also anything subsumed therein, as well as endpoints.

The ex-vivo skin screening methods/models generally comprise one or more of the following: collecting surgical waste donor tissue, preparing the tissue for culturing, treating the tissue with test agent applied topically or within the culture medium, culturing the tissue for a period of time, and measuring one or more endpoints of interest (e.g., gene transcription, etc.).

Non-limiting aspects and examples of various embodiments of ex-vivo skin screening methods will now be described. While various embodiments are described hereafter in the context of controls, culturing conditions, gene transcriptomics, processing of skin tissue, mRNA processing, it will be appreciated that the details provided herein are intended to be illustrative only and that many modifications, additions, deletions, and other changes are possible in view of the teachings herein.

I. Donor Tissue

In some embodiments, donor tissue such as human surgical waste tissue from any of a wide variety of surgical procedures (e.g., abdominoplasty or full body lift procedures) may be used a source of human skin samples. Upon receipt, the donor tissue may be stored at a temperature below room temperature (e.g., between 2° C. and 10° C. or between 2° C. and 6° C.) for up to 24 hours. Storage at cooler temperatures can pause development of inflammation, which will resume upon tissue re-warming.

The donor tissue or human skin samples obtained therefrom may be processed to remove the subcutaneous layer. Removal of the subcutaneous layer can improve absorption of the media into the skin sample during culturing and may also enable an ex vivo skin model that is suitable for either topical or media delivery of test agents. The skin sample may then be further subdivided into smaller pieces (e.g., 1.25 mm×1.25 mm square) which can be placed into a multi-well tissue plate. Some of these smaller pieces may be dosed with a positive control, while others may be dosed with the test agent(s) to be screened. In some embodiments, some of the smaller pieces may not be treated to provide a control. The skin samples may be positioned in the plate wells with the dermis side down over an iso-osmotic solution to keep the dermis moist and the epidermis dry. A non-limiting example of a suitable iso-osmotic (or isotonic) solution can be Dulbecco's Modified Eagle Medium ("DMEM"). In some embodiments, the tissue samples may be placed in non-osmotic (non-isotonic) solution. Optionally, anti-mycotic or antibacterial reagents may be included in the solutions or applied to the samples separately. A non-limiting example of ex vivo tissue preparation is described in Example 1 below. In some embodiments, the skin samples may be placed on a porous or semi-porous membrane (e.g., a Millipore® brand, eight micron, six-well membrane insert) within the plate wells, which may improve the viability of the tissue sample during culturing. It may be desirable to select a membrane that permits the media to pass through it at a particular rate, based on the size and/or type of skin sample.

FIG. 1 illustrates the viability of ex-vivo skin tissue using different culture methods to demonstrate the potential benefit of culturing on a suitable membrane. Viability is assessed by a conventional MTT (3-(4,5-Dimethylthiazol-2-yl)-2,5-diphenyltetrazolium bromide) assay, which is known in the art. Ex-vivo skin punches 4 mm in diameter were place directly in media (i.e., submerged) or placed on a membrane above the media such that the media feeds the tissue via capillary action through the membrane from below. In addition, 1 cm$^2$ skin samples were cultured on a membrane to illustrate the important role that sample size can play in some embodiments (e.g., longer experiments). Two time points at 24 and 96 hours are shown. Assay controls for baseline viability level (baseline) and a background tissue that has been frozen and thawed 3 times (total kill) are also shown. As illustrated in FIG. 1, the viability of the cells cultured on the membrane decreased significantly less than the cells placed directly in the media between 24 hours and 96 hours. In addition, the 1 cm$^2$ samples showed significantly improved viability between 24 and 96 hours when compared to the 4 mm punch biopsy samples.

II. Ex Vivo Tissue Biology and Selection of Genes

Figure 2:
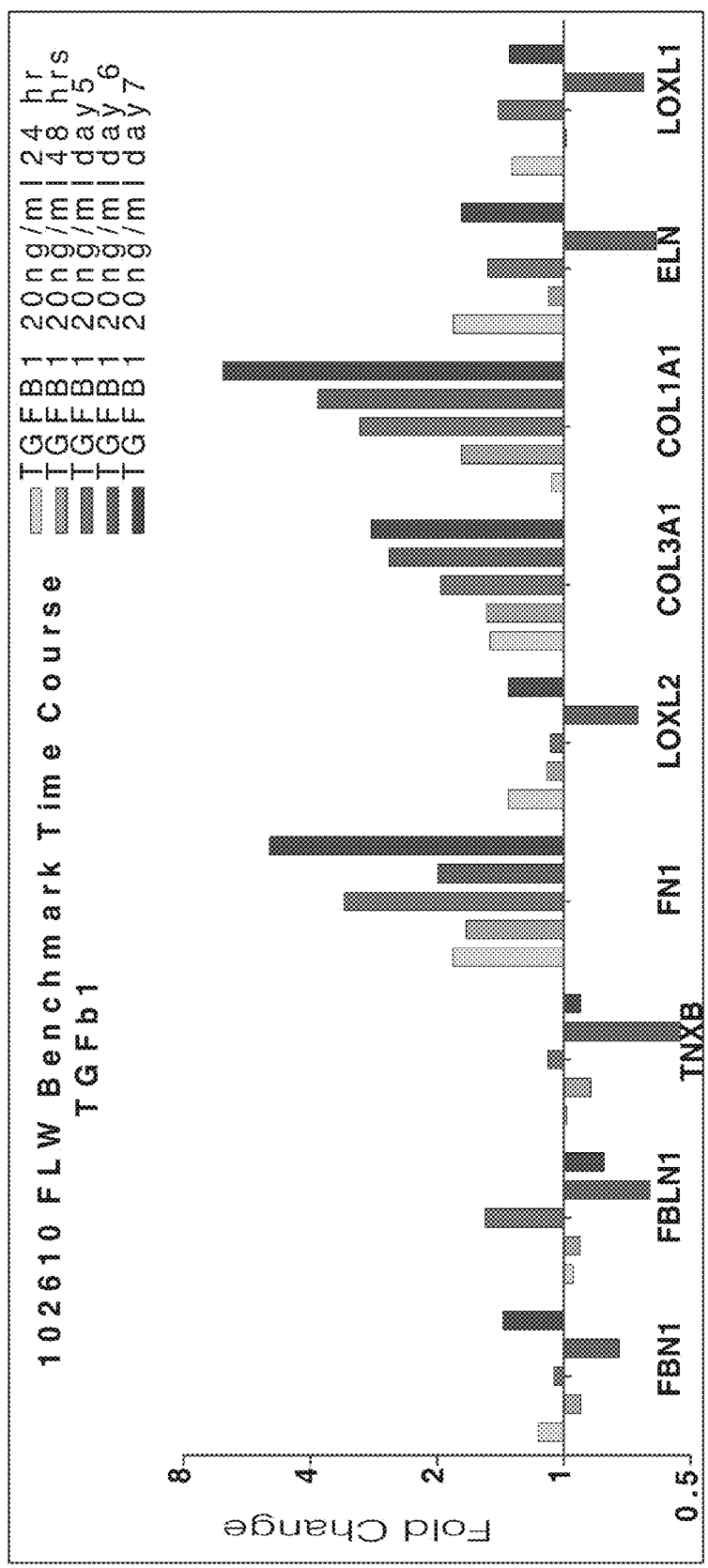
FIG. 2 is a bar graph illustrating fold changes in ex vivo skin tissues for a dermal gene panel over a time course of 7 days from treatment with TGFβ-1.

One uncertainty in the development of an ex vivo screening method and model is whether and/or to what extent donor tissue can be suitably regulated after surgical extraction. To answer this question, regulation of a set of genes by an endogenous gene stimulative compound was studied. TGFβ-1 was chosen as the stimulative compound, as it is a known regulator of dermal matrix genes associated with the production of collagen and elastin. Referring to FIG. 2, the response of a dermal gene panel is shown for tissue samples from a single donor which were subjected to media applied TGFβ-1 (20 ng/ml) over a time course between 24 hrs and 7 days. Over the time course, the donor tissue exhibited a good response with respect to FN1, COL1A1 and COL3A1, which are increasingly up-regulated over the time period. This tends to confirm that it is possible for ex vivo tissue to be suitably regulated over a relevant time course after surgical extraction.

While validating that ex vivo tissue can be suitably regulated by a relevant gene stimulative compound is a significant development, another step in the development of an ex vivo screening method/model is the identification and/or selection of an appropriate set of markers for use in the screening methods and models that can be appropriately regulated over the culturing time period. Referring to FIG. 3, a list of some genes suitable for inclusion in the ex vivo screening methods and models are listed. This list comprises genes believed to be involved in various pathways associated with skin aging and/or whose regulation may beneficially provide a skin anti-aging benefit. As used herein, skin anti-aging benefits include, but are not limited to, improving skin appearance and/or feel by providing a smoother, more even appearance and/or feel; increasing the thickness of one or more layers of the skin; improving the elasticity or resiliency of the skin; improving the firmness of the skin; and reducing the dull appearance of skin, improving the hydration status or moisturization of the skin, improving the appearance of fine lines and/or wrinkles, improving skin texture or smoothness, improving skin exfoliation or desquamation, plumping the skin, improving skin barrier properties, improving skin tone, reducing the appearance of redness or skin blotches, and/or improving the brightness, radiancy, or translucency of skin. The genes listed in FIG. 3 can be loosely grouped into five panels (e.g., a dermal gene panel, a growth factor/senescence gene panel, a retinoid metabolism gene panel, a basement membrane gene panel, and an epidermal gene panel).

FIG. 4 illustrates a heat map of the fold change of some of the genes from FIG. 3 following media dosing of ex vivo tissue samples (N=6 per material) incubated at 33° C. and 55% relative humidity with four materials over a 7 day time course. Cross-hatching is provided in some of the cells of the table in FIG. 4 to indicate statistically significant up-regulation (p value≤0.05 and p value≤0.1) and statistically significant down regulation p value≤0.05 and p value≤0.1). In addition to TGFβ-1, three exogenous materials believed to provide one or more in vivo, anti-aging skin benefits were tested. The three exogenous materials tested were a vitamin B3 compound (i.e., niacinamide), a peptide (i.e., PAL-KT brand peptide (palmitoyl-lysine-threonine)), and an olive oil extract (i.e., OLIVEM 460 brand olive oil extract). Niacinamide is believed to provide a number of cosmetic skin care benefits (see, e.g., Bissett el al. "Niacinamide: A B Vitamin that Improves Aging Facial Skin Appearance" and Draelos "Clinical Situations Conducive to Proactive Skin Health and Anti-Aging Improvement"). Certain peptides such as PAL-KT are also recognized as materials that can provide skin anti-aging benefits, such as an improvement in the appearance of fine lines and wrinkles (see, e.g., In Vitro Biomarker Responses to a New Anti-Aging Peptide, PAL-KT, Osborne et al, American Academy of Dermatology 67$^{th}$ Annual Meeting Media Resources, 2009). Certain olive oil derivatives such as OLIVEM brand olive oil derivatives are also believed to provide anti-oxidant activity, which may lead to protection against environmental assaults (see, e.g., Skin Biomarkers Confirm the Anti-Oxidant Activity of Olive Derivatives and Yeast Ferment Filtrate, Finlay et al., P&G 67$^{th}$ Annual Meeting of American Academy of Dermatology (2009)).

At the end of 4 and 7 days, two 4 mm punch biopsies were removed from each of the tissue samples for RNA isolation followed by PCR analysis. Several observations are notable from a review of the data shown in FIG. 4. It appears there is an increase generally in the number of significantly regulated genes over the time course, indicating what appears to be an appropriate biological response to TGFβ-1 (a material believed to either directly stimulate dermal matrix genes) and the three exogenous materials, which are believed to provide a skin anti-aging benefit. For example, COL4A1 and LAMA5 are up-regulated over the time course, consistent with dermal collagen regulation and what appears to be an appropriate biologically response to the tested materials. The olive oil extract and peptide both up-regulated TGFβ-2 and TGFβ-3, which are believed to increase expression of TGFβ-1 by fibroblasts leading to collagen production. Again, this appears to be an appropriate biological response to these materials. Thus, it seems that the ex vivo tissue biology and the genes listed in FIG. 4 are responding in an appropriate manner over the time course consistent with the regulation that might be expected from the tested materials.

Figures 5A, 5B:
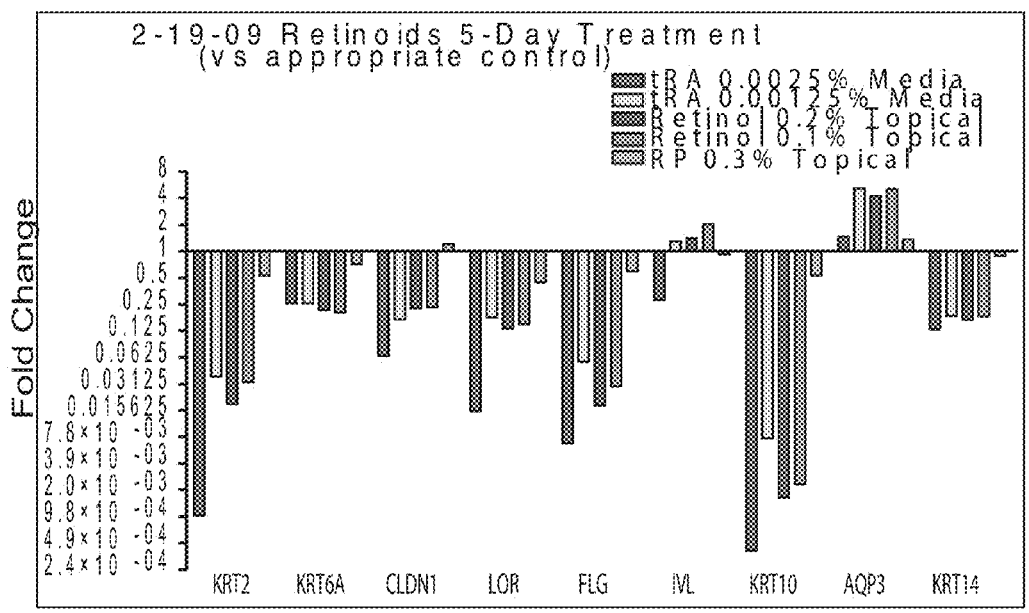
FIG. 5A is a bar graph illustrating fold changes in ex vivo skin tissue samples for some of the genes listed in FIG. 3 over a 5 day time course.
FIG. 5B is a table illustrating the p-values for the fold change data shown in FIG. 5A.

Referring to FIG. 5A, a bar graph illustrates the fold change (compared to an untreated control) for the epidermal gene panel of FIG. 3 following media dosing with trans-retinoic acid (tRA), retinol, or retinol propionate (RP) over a 5 day time course. FIG. 5B is a table of the p-values illustrating the fold change data of FIG. 5A. The doses were applied over a 5 day time course during which tRA was media applied while retinol and retinol propionate were topically applied to the ex-vivo tissue samples (N=6 per material) incubated at 33° C. and 70% relative humidity. At the end of 5 days, two 4 mm punch biopsies were removed from each of the tissue samples for RNA isolation followed by PCR analysis. From this data, it appears that the test compounds appropriately regulated the epidermal gene panel. For example, KRT10 and FLG are significantly down-regulated and AQP3 is up-regulated. In addition, the relative fold change of tRA>retinol>retinol propionate appears to be appropriate. These observations indicate what appears to be an appropriate biological response to vitamin A compounds over the 5 day time course. As used herein, "vitamin A compounds" refers to vitamin A compounds, their precursors and metabolites. Thus, it seems that the ex vivo tissue biology is responding in an appropriate manner over the time course consistent with the regulation that might be expected from the tested materials. While the epidermal gene panel is largely down regulated by the vitamin A compounds thereby indicating a proliferative response, it is understood that up-regulation of one or more of these genes in the ex-vivo models and methods may occur from other materials that induce improved barrier and/or stratum corneum structures.

FIGS. 6A, 6B, and 6C provide heat maps illustrating the fold change for the gene panel of FIG. 3 over a 7 day time course following media dosing with the tRA and retinol propionate. The cells in FIGS. 6A, 6B, and 6C are cross-hatched in the same way as the cells in FIG. 4 (i.e., see the legend provided in FIG. 4). The tRA was media applied and the retinol propionate was topically applied to the ex-vivo tissue samples (N=6 per material), which were incubated at 37° C. and 50% relative humidity. At the end of 48 hours, 5 days and 7 days, two 4 mm punch biopsies were removed from each of the tissue samples for RNA isolation followed by PCR analysis. It can be seen that a correlated regulation, meaning both tRA and retinol propionate showed similar patterns of regulation, of the retinoid gene panel appears between Day 5 and Day 7. However, tRA stimulates a stronger response of these retinoid metabolism genes than RP. By day 7 Cyp26B1, a p450 enzyme that breaks down excess retinoid, is strongly up-regulated by both materials. Also, by day 7 both materials strongly up-regulate CRABP2, RARG, and CEBPA, a retinoid transporter, receptor, and transcription factor. These genes are all important in retinoic acid-mediated regulation of human skin growth and differentiation. Again, the data show what appears to be an appropriate biological response to the tested materials. Thus, it appears that the various genes listed in FIG. 3 may be appropriately regulated in ex-vivo skin tissue, as demonstrated by testing with known stimulative endogenous and exogenous materials.

III. Culturing Conditions: Time, Temperature, Humidity

One development in the ex vivo screening methods and models described herein is the investigation/identification of appropriate culturing conditions for the screening methods and models for which it is possible to appropriately regulate the genes of interest. Importantly, the ex-vivo tissue culturing conditions (e.g., time, temperature and humidity) can affect the performance of the ex vivo models and screening methods, including the responsiveness of one or more of the genes listed in FIG. 3. While certain ranges for temperature, time and humidity are discussed below, it will be appreciated that these ranges and combinations of conditions can be varied from what is described. The conditions of time, temperature and humidity described herein may be preferably combined in whole or part to achieve what may be the best set of culturing conditions. A non-limiting example of ex vivo tissue culturing for the screening models and methods described herein is provided in Example 2.

Time

The culturing time period can affect the directionality and/or significance of the gene regulation in ex vivo skin tissue. For example, referring again to FIG. 4, the data appears to show that many of the genes are down regulated and/or not statistically up-regulated for the tested materials compared to untreated controls at Day 4. However, many more of these same genes are up-regulated at Day 7 across the tested materials, and many more genes are up-regulated with statistical significance at Day 7 (compared to Day 4). Referring to FIGS. 7A and 7B, heat maps illustrating the fold changes observed in the dermal gene panel after 5 days and 7 days are provided, but with tissue from a different donor (relative to the donor tissue used to generate the data illustrated in FIG. 4). The cells in FIGS. 7A and 7B are cross-hatched in the same way as the cells in FIG. 4 (i.e., see the legend provided in FIG. 4). By Day 7, there were fewer genes down-regulated than at Day 5, and there was an overall increase in the number of statistically significant genes that were up-regulated, which again validates that a more robust response was observed by Day 7 and likely occurs between Day 5 and Day 7.

Figures 8A, 8B:
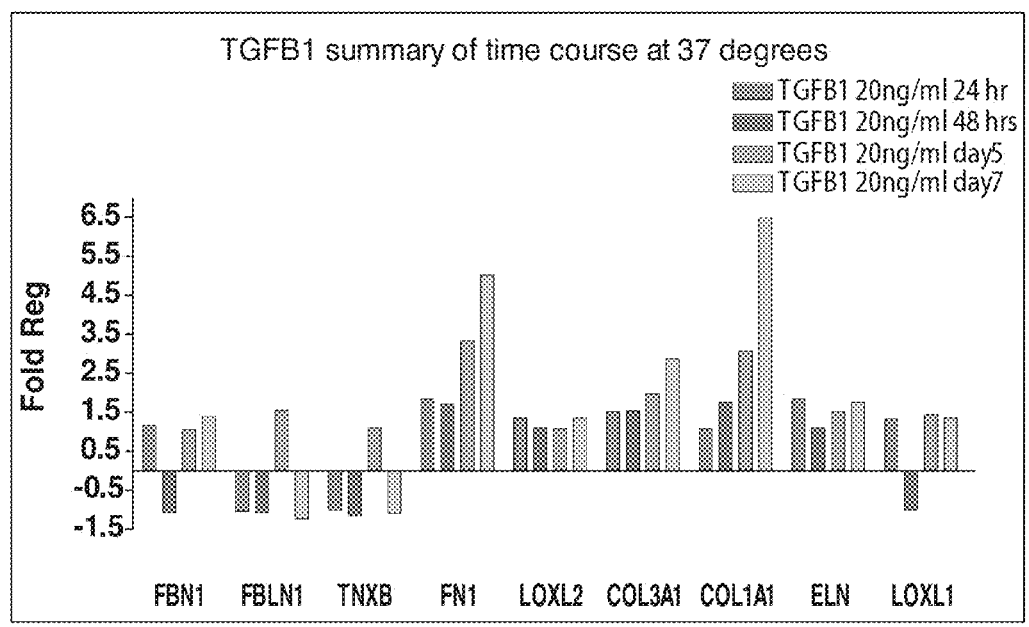
FIG. 8A is a heat map illustrating fold changes in ex vivo skin tissue samples from a single donor over a 7 day time course from media application of TGFβ-1.
FIG. 8B is a bar graph illustrating the fold changes shown in FIG. 8A.

Referring to FIGS. 8A and 8B, fold change data over a 7 day time course is illustrated following media application of 20 ng/ml of TGFβ-1 to ex vivo tissue from a single donor. The tissue was incubated at 37° C. for 1 to 7 days at 50% relative humidity. The cells in FIG. 8A are cross-hatched in the same way as the cells in FIG. 4 (i.e., see the legend provided in FIG. 4). FIG. 8B is a bar graph illustrating the data from FIG. 8A. While some of the genes (e.g., FN1, LOXL2, COL3A1, ELN, and LOXL1) were significantly regulated at 24 hrs, the most robust response occurred between Day 5 and Day 7, which appears consistent with the data previously discussed.

Referring again to FIGS. 6A, 6B, and 6C, the fold change data from a single donor over a 7 day time course is shown for media application of tRA and topical application of retinol propionate. While some of the genes of the retinoid gene panel were down-regulated by Day 5, there was a much more pronounced and correlative regulation pattern between tRA and retinol propionate by Day 7. For example, by Day 7, CYP26A1, ALDH1A2, RDH10, RARRES1, and LRAT were down-regulated with statistical significance across both materials compared to Day 5.

Based on the foregoing, it is believed that a culturing time period from about 5 days to about 19 days or from about 6 days to about 10 days or from about 6 days to about 8 days is preferred, although shorter or longer time periods may be appropriate in some circumstances.

Temperature

The culturing temperature can also affect the pattern and magnitude of the gene regulation in ex vivo tissue samples. Referring to FIGS. 9A and 9B, heat maps illustrate the fold changes for nine dermal genes for five different donor tissue samples incubated at 33° C. for 7 days and 50% relative humidity and five different donor tissue samples incubated at 37° C. for 7 days at 50% relative humidity. The cells in FIGS. 9A and 9B are cross-hatched in the same way as the cells in FIG. 4 (i.e., see the legend provided in FIG. 4). The tissue samples were treated with a media supplied dose of 20 ng/ml of TGFβ-1. The number of statistically significant genes up-regulated at 37° C. increased dramatically over the number of statistically significant genes regulated at 33° C., although FN1, COL1A1, and COL3A1 for example were significantly up-regulated at 33° C. across a number of donors. In contrast, ELN and LOXL2 for example did not show statistically significant up-regulation across a majority of donors at 33° C. but did at 37° C.

Referring to FIG. 10, two more heat maps illustrate fold changes for nine dermal genes following incubation at 33° C. and 37° C. for 7 days at 50% relative humidity. The tissue samples were treated with media supplied doses of 0.2% niacinamide and 0.001% of an olive oil extract. Notably, the olive oil extract mostly down-regulated the dermal genes at 33° C. and predominantly up-regulated the dermal genes at 37° C., with a marked overall increase in the number of statistically significant genes that were up-regulated at 37° C. compared to 33° C. This data tends to further support the observation that higher culturing temperatures are more preferred to generate an appropriate transcriptomic response to the tested materials, although tissue viability tends to decrease as temperature increases.

Based on the foregoing, in some embodiments, a culturing temperature from 33° C. to 40° C., from 35° C. to 40° C., or even from 36° C. to 38° C. may be suitable, although individual gene responses can vary within these ranges and lower culturing temperatures (e.g., down to about 32° C.) may be useful for observing some genes.

Humidity

Figure 11:
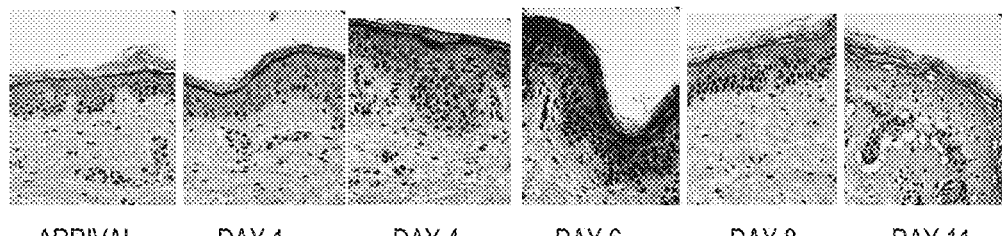
FIG. 11 is a series of photo micrographs of ex-vivo skin tissue cultured at 37 C at 95% relative humidity over a time course of 11 days.
Figure 12:
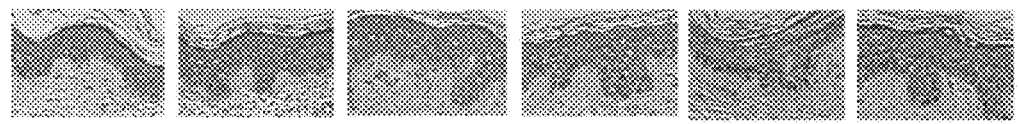
FIG. 12 is a series of photo micrographs of ex-vivo skin tissue cultured at 37 C at 50% relative humidity over a time course of 10 days.
Figure 13:
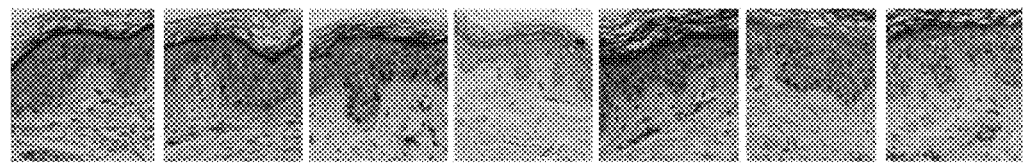
FIG. 13 is a series of photo micrographs of ex-vivo skin tissue cultured at 33 C at 70% relative humidity over a time course of 19 days.
Figure 14:
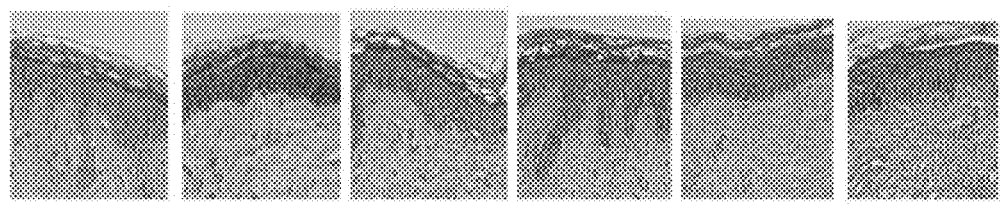
FIG. 14 is a series of photo micrographs of ex-vivo skin tissue cultured at 33 C at 70% relative humidity over a time course of 11 days.

Longevity of the ex vivo tissues can be improved under conditions of reduced humidity. It is believed to be possible to culture at relatively higher temperatures by reducing the humidity and still maintain tissue viability and/or consistent gene regulation. Referring to FIG. 11, an ex-vivo skin tissue cultured at 37° C. and 95% humidity is shown from the date of arrival out to 11 days in minimal DMEM (minimal DMEM refers to DMEM with as few components added as possible to minimize additional variables). As illustrated in FIG. 11, the tissue morphology degraded substantially over the 11-day time period. In comparison, FIG. 12 illustrates an ex-vivo tissue sample cultured at 50% humidity and 37 C out to 10 days, wherein the morphology of the tissue remains largely intact over this time period. Comparing FIGS. 11 and 12, it can be seen that the morphology of the tissue is much improved at the lower humidity condition. In fact, it appears possible to culture ex-vivo skin tissue out to at least 19 days (at, for example, 70% humidity and 33° C.) while still maintaining tissue viability and/or morphology (see, e.g., FIG. 13). Referring to FIG. 14, the histology of an ex-vivo tissue sample cultured at about 70% relative humidity and about 33° C. for about 11 days is shown.

In some embodiments, a relative humidity of less than 100% humidity is provided. For example, the ex vivo human skin tissue sample may be cultured at a relative humidity of from 40% to 90% or from 50% to 70%.

IV. Positive Controls

An additional development in the ex vivo screening methods and models is the identification and/or usage of one or more positive controls to identify tissue samples that are appropriate responders for inclusion in the screening methods/models. In some embodiments, the positive control should have a robust signal to noise ratio and result in an appropriate response in a large enough portion of the donor population to effectively distinguish between tissue that is appropriately regulated and non-responders that should be discarded, thereby minimizing false positives, false negatives, or otherwise potentially inaccurate observations. This can be an important factor in a commercial screening method/model where consistency across a large donor population is useful. In some embodiments, the positive control provides statistically significant regulation of 2 or more genes in greater than 50%, 60%, or 70% of the donor tissue and/or less than 90% or less than 80% of the donor tissues. This level of success is useful for screening hundreds of test agents and requires a level of consistency beyond that of primary academic research studies which typically require minimal sample sizes for statistical comparisons. Also, donor to donor variability relating to the state of the tissue sample may also be addressed in the screening method.

In some embodiments, the positive control may be a known anti-aging material (e.g., niacinamide, a peptide, etc.) or an endogenous gene stimulative compound (e.g., TGFβ-1, TGFβ-2, TGFβ-3). While TGFβs are known regulators of dermal matrix genes, it was not clear at the outset how ex vivo tissue would respond to TGFβ (or other potential positive controls) over the culturing time periods/temperatures and/or whether a sufficient portion of the ex-vivo donor population would be sufficiently responsive to enable an ex-vivo screening method and model. Referring again to FIGS. 2, 4, 7 and 8, the dermal genes exhibited a strong, consistent, up-regulation response to media supplied TGFβ-1, thereby indicating that a TGFβ compound might be used as a satisfactory positive control. Referring to FIG. 15, a heat map of the fold changes in eight different donor tissues is shown following media application of 20 ng/ml TGFβ-1 over a time course of 11 days at a temperature of 33° C. and 70% relative humidity. The cells in the chart of FIG. 15 are cross-hatched in the same way as the cells in FIG. 4 (i.e., see the legend provided in FIG. 4). While there is some variability among the samples, the data surprisingly show that 80% of the donor tissues had statistically significant up-regulation of at least FN1, COL1A1, and ELN. Donor tissue #6 was a non-responder and normally may not be considered good enough to draw any valid conclusions if used in a screening assay (e.g., an insufficient number of genes are up-regulated regulated and/or only FN1 was significantly up-regulated). Donor tissue #5 could be considered a moderate responder, since there is statistically significant up-regulation of ELN, COL1A1, FN1, LOXL1, and FBN1. In addition, 7 of the 9 genes were up-regulated. As such, this tissue sample would qualify as tissue capable of dermal regulation and therefore would be considered valid for use in a screening method. Donor tissues #7 and #9 could be considered strong responders, since 8 or 9 of the genes are up-regulated (of which 7 are statistically significant). From the foregoing, it appears that TGFβ can provide sufficient and/or statistically significant regulation of the dermal genes in a significant portion of the donor tissues. While it is believed that an endogenous dermal gene regulator, such as a TGFβ, can be used as a positive control, it is contemplated that an exogenous material may also be used as a positive control as demonstrated, for example, by the regulation patterns presented in FIG. 4.

In other embodiments, the positive control may be a vitamin A compound. In some embodiments, the vitamin A compound is a metabolite of a vitamin A compound, such as tRA. In some embodiments, the positive control may be a material known to provide a skin anti-aging benefit, such as a peptide, a vitamin A compound, a vitamin B3 compound (e.g., niacinamide) or other well known materials.

In some embodiments, a donor tissue is acceptable for inclusion in an ex-vivo screening method and/or model where at least 2, 3, 4, 5, 6, 7, 8 or more of the genes selected from FIG. 3 are regulated in an appropriate direction for providing a skin anti-aging benefit by a positive control. For example, the dermal gene panel might be generally up-regulated by TGFβ-1 in an acceptable donor while the retinoid metabolism gene panel might be generally down-regulated by tRA in an acceptable donor. In some embodiments, the directionality is statistically significant and/or the fold change is greater than 1, 2, 3, 4, or 5. In some embodiments, the at least 3, 4 or more genes are selected from the group consisting of FBN1, FBLN1, TNXB, FN1, LOXL2, COL3A1, COL1A1, ELN, LOXL1, ALDH1A2, RDH10, RARRES1, and LRAT In some embodiments, the at least 3, 4, 5, 6, 7, 8 or more genes comprise one or more of FN1, COLA1, and ELN.

In some embodiments, a second human skin tissue sample is screened with a positive control to validate that the genes of interest may be properly regulated and that the donor tissue is capable of providing a valid response. The second human skin tissue sample can be derived from the same human donor surgical waste tissue as the other skin samples used in the screening method.

V. Gene Transcriptional Patterns Useful for Identifying a Material as Providing a Skin Benefit Still another development in the ex vivo screening methods and models is the identification of gene transcriptional patterns that may identify a test agent as potentially providing an in vivo benefit. Based on the patterns presented in the various figures herein, in some embodiments, a test agent may be identified as potentially providing an in vivo skin anti-aging benefit where the transcriptional profile of 1, 2, 3, 4, 5, 6, 7, 8, 10, 12, 14, 16 or more of the genes listed in FIG. 3 are regulated in a manner similar to the regulation induced by the positive control. For example, the genes of interest might be regulated in the same direction by the test agent and the positive control and/or the magnitude (and possibly the statistical significance of) of the fold changes might be the same or similar. In other embodiments, the gene(s) of interest are regulated in an appropriate direction for providing a skin anti-aging benefit. In some embodiments, the regulation may be statistically significant (e.g., p≤0.1 or 0.05), and in some embodiments the fold change may be greater than 1, 2, 3, 4, 5 or more. In some embodiments, the fold change may be greater than that observed with the positive control. For the genes shown in FIG. 4, one direction of regulation to provide a skin anti-aging benefit is up-regulation compared to an untreated tissue sample. For the retinoid metabolism gene panel shown in FIG. 3, one direction of regulation for many of the genes to provide a skin anti-aging benefit is down regulation (when a retinoid type response is sought). For the epidermal gene panel shown in FIG. 3, the direction of regulation may be either up or down depending on the response sought (e.g., a retinoid might generally lead to down regulation)

In some embodiments, the genes of interest are associated with the formation of connective and extracellular matrix tissues, including collagen, elastin, microfibrils, etc. In some embodiments, these genes are selected from the group consisting of FBN1, FBLN1, TNXB, FN1, LOXL2, COL3A1, COL1A1, ELN, LOXL1, TGFB2, TGFB3, TGFBR1, TGBR2, TGFBR3, CTGF, COL4A1, and LAMA5, and in some embodiments, the genes of interest are selected from the group consisting of FBN1, FBLN1, TNXB, FN1, LOXL2, COL3A1, COL1A1, ELN, and LOXL1. In some embodiments, the skin anti-aging benefit is related to one or more of improving the appearance of fine lines and/or wrinkles, improving skin sagging, and texture.

Referring to FIG. 16, a heat map of fold changes for tissue samples from a single donor are shown. The tissue samples were incubated at 7 days at 37° C. at 50% relative humidity and media dosed with TGFβ-1 (as a positive control) and a test agent. The donor tissue was a good to strong responder as shown by the pattern of regulation associated with the positive control (see legend in FIG. 4), so the results may be considered valid. The test agent up-regulated all nine of the listed dermal genes, of which eight were up-regulated in a statistically significant manner. Some of the genes (e.g., ELN, LOXL1, and LOXL2) were up-regulated by the test agent to a larger degree than by the positive control. Based on the pattern of regulation, the test agent qualifies as a material that could provide an anti-aging skin benefit. The test agent was placed in a thirteen week randomized, double blinded, vehicle controlled, split face fine line and wrinkle study. The test agent was formulated in a composition at a concentration of 3.5% by weight of the composition. Two hundred thirty-nine test subjects were enrolled in the study, and eighty-eight percent of the subjects completed the study. The primary endpoint measured was fine line and wrinkle improvement via expert grading of images taken at weeks 8 and 12 versus a baseline image. Image analysis of wrinkle area fraction was a secondary endpoint that was measured. The test agent improved the appearance of fine lines and wrinkles by a statistically significant amount compared to baseline according to the expert grading of the images. The test agent also reduced calculated wrinkle area fraction after 12 weeks by a statistically significant amount compared to a 3% glycerin control. The in vivo test results indicate that the test agent can provide a skin anti-aging benefit.

The ex vivo models and methods herein may surprisingly be used to determine whether a combination of two or more agents might provide a synergist transcriptional response. As used herein, the phrase synergistic transcriptional response means a transcriptional response different, or perhaps even substantially different, from the transcriptional response provided by the test agents individually. For example, one synergistic response is regulation of a gene in one direction by the test agents individually and regulation of the gene in the opposite direction by the combination of test agents. Another synergistic response is where the transcriptional response from the combination of test agents is additively greater than or less than the addition of the individual transcriptional responses from each test agent.

Referring to FIG. 17, artichoke leaf extract, carob fruit extract, and a combination of artichoke leaf and carob seed extracts, were evaluated according to the methods described herein. The fold-increase/decrease in expression, versus an untreated control, was determined for the epidermal gene panel set forth in FIG. 3 for ex vivo tissue from a single donor over a 7 day time course incubated at 37° C. at a relative humidity of 55%. The test agents were applied topically. A positive fold increase indicates the desirable up-regulation of that gene, which in this gene set can be important for improving epidermal differentiation, skin barrier and moisture status, and thus a positive anti-aging benefit. As shown in FIG. 17, the transcriptional response from the combination of artichoke leaf extract and carob fruit extract are, generally, greater than would be expected from the addition of the individual transcriptional responses from each test agent (i.e., a synergistic response). In addition, some genes were both down-regulated by the test agents individually but up-regulated by the combination (see, e.g., KRT10, KRT6A, CLDN1, and KRT10).

Referring to FIG. 18, an olive oil extract, an artichoke leaf extract, and a blend of these extracts were evaluated according to methods described herein. The cells in the table of FIG. 18 are cross-hatched in the same way as the cells in the table of FIG. 4 (i.e., see the legend provided in FIG. 4). The fold-increase/decrease in expression, versus an untreated control, was determined for the dermal gene panel set forth in FIG. 3 for ex vivo tissue from a single donor over a 7 day time course. The skin samples were incubated at a temperature of 37° C. and a relative humidity of 55%. The test agents were applied topically to the skin samples. The heat map shown in FIG. 18 illustrates the rather limited response of this donor skin to both extracts individually. However, when the two extracts are combined, there is change in significance and directionality as shown in FIG. 18. This is even more strongly evident when the concentration of the olive oil extract is increased to 0.001%. This is another example of identifying actives that may synergistically provide anti-aging benefit.

VI. mRNA Processing mRNA processing may include pulverizing or homogenizing human skin tissue samples to obtain DNA, RNA, or other materials for analysis. The methods and models described herein can involve analysis of RNA from full or partial human skin tissue samples or from simple cell types removed from such samples. Dermal and epidermal layers may be removed and analyzed separately or together. Transcriptional profiles can be generated from such individual cells, layers, or from multiple cells, layers, parts (or in whole) of the human skin tissue sample or samples. Gene expression measurements may be made using any suitable profiling technology. For example, the mRNA expression of the genes of interest may be determined using microarray techniques. Other emerging technologies that may be used include RNA-Seq or whole transcriptome sequencing using NextGen sequencing techniques. As used herein, the term "microarray" refers broadly to any ordered array of nucleic acids, oligonucleotides, proteins, small molecules, large molecules, and/or combinations thereof on a substrate that enables gene expression profiling of a biological sample. Non-limiting examples of microarrays are available from Affymetrix, Inc.; Agilent Technologies, Inc.; Illumina, Inc.; GE Healthcare, Inc.; Applied Biosystems, Inc.; Beckman Coulter, Inc.; etc.

A non-limiting example of mRNA processing is provided in Example 3.

VII. Screening Methods and Models

As previously discussed, human donor tissue can be derived from surgical waste tissue. In those embodiments where the surgical waste tissue is divided into at least first and second human skin samples, the subcutaneous fat layer can be (although does not need to be) removed before dividing the tissue into individual samples. In some embodiments where the subcutaneous fat layer is removed, the human skin samples may be composed primarily of an epidermal layer and dermal layer. The skin samples may be dosed with a positive control material, one or more test agents, or remain untreated for use as comparative controls (meaning not treated with either the positive control or the test agent(s)). In some embodiments, all or only a portion of a tissue sample may be dosed with the test agent(s) or the positive control. As previously discussed, multiple test agents and combinations of test agents may be screened to identify synergistic transcriptional responses.

In some embodiments the screening method may be used in repetition. The screening method can involve repeating one or more of the following: 1) providing a skin sample, 2) contacting a skin sample with a positive control or a test agent, 3) generating a transcriptional profile for a skin sample treated with a positive control and/or a test agent, 4) comparing the transcriptional profile of a skin sample treated with a positive control to the transcriptional profiles of a skin sample treated with a test agent, and 5) identifying a test agent as suitable for providing an anti-aging benefit. The skin samples used in the foregoing repetitions may be from different donors. Each repetition may also involve a different test agent and/or different positive control. A plurality of test agents may be screened according to the present method. In some embodiments, greater than about 5, 10, 25, 50, 100, 200, 400, 800 and/or less than about 1000, 2500, 5000, 10000, 20000, or 50000 test agents may be screened. In some embodiments, the effect of 2, 4, 6, 10, 25, 50, 100, 200, 500 or more of the test agents screened using ex-vivo tissue from different donors may be compared to each other to identify which test agents provide, relative to each other or the positive controls, the best regulation of the genes of interest to provide a cosmetic anti-aging skin benefit.

The test agent or positive control may be applied topically or via the media. For topical applications, the ex-vivo skin tissue may be dried prior to application of the agent. In some embodiments, the test agent may be topically applied daily or at another suitable interval as desired (e.g., hourly, every 4, 6, 8, 10, 12, 14, 16, 10 or 20 hours, every other day, or on specific days over multiple weeks). Test agent herein be in the form of any material suitable for application to an ex vivo tissue sample, including but not limited to any compound, chemical substance, ingredient, extract, excipient, mixture, formulation, or composition. It may be desirable to select test agents that are suitable for incorporation into personal care compositions. For example, botanical extracts, which may comprise a wide variety of fractions or compounds, are considered test agents herein and are known, in some instances, to be incorporated into cosmetic compositions.

The ex-vivo skin tissue may be fed based on its cellular metabolic rate; feedings can be multiple times a day, every day, every other day, or on specific days throughout a multi-week period (such as 2, 3, or more). The feedings can be temperature dependent, such as daily feedings for cultures maintained at a temperature of 37 C, or every other day for cultures maintained at a temperature of 33 C.

Ex vivo skin tissue models may comprise one or more ex-vivo skin tissue samples cultured according to one or more of the methods described herein. In one embodiment, the model comprises a cultured ex-vivo skin tissue sample derived from human skin surgical waste tissue that has been treated with a TGF compound as a positive control, wherein regulation of 2 more genes in a directionally appropriate manner indicates that the human surgical waste tissue is acceptable for screening a test agent. In some embodiments, the 2 or more genes are genes known or believed to be regulated by the TGF compound. In some embodiments, the 2 or more genes are selected from the genes listed in FIG.

4. In some embodiments, the 2 or more genes are selected from the dermal gene panel of FIG. 3. In some embodiments, the directionally appropriate regulation comprises up-regulation of the 2 or more genes. The model may further comprise one or more additional human skin samples derived from the human surgical waste tissue, which may be cultured in a manner suitable for screening a test agent.

The screening methods described herein may also be combined with other screening methods to provide a tiered screening process. Tiered screening methods are typically associated with assays of increased complexity at each tier. Each tier of the tiered screening method provides additional data thereby permitting conclusions to be drawn that more accurately focus on the potential of a test agent to provide an anti-aging skin benefit. Therefore, higher tiers in the method are associated with a lower number of possible agents that have a higher probability of being effective. Tiers may, in some embodiments, advance as follows: enzyme assays, cell-based cultures, in vitro assays, and one or more ex-vivo skin assays of the present invention. Enzyme assays involve an analysis of protein functions, cell-based cultures involve simply cell cultures primarily in culture plates, and in vitro assays involve more complex culturing conditions with combined cell-types. Initial tiers can be completed relatively more quickly with higher outputs, while advanced tiers typically involve additional time and lower thru-put. An in-depth analysis of each tier provides end data allowing increased probabilities of success for the test agents.

VIII. Cosmetic Compositions.

Because of the desirability of providing various cosmetic skin anti-aging benefits to a consumer, it may be beneficial to incorporate a test agent identified by one or more of the screening methods and models described herein into a cosmetic composition suitable for topical application to skin. In addition to formulating a cosmetic composition for in vivo testing, cosmetic composition may be repeatedly manufactured or formulated for commercial distribution. The cosmetic composition may be formed by combining a test agent(s) identified by the models and/or screening methods described herein with a dermatologically acceptable carrier. In some embodiments, commercial or bulk quantities of the cosmetic composition may be manufactured. For example, the cosmetic composition may be manufactured by a batch process where a relatively large volume of ingredients are combined in one or more vessels prior to depositing or storing in a plurality of containers or packages suitable for commercial/retail distribution. In some embodiments, the ingredients may be combined in whole or part in the product containers/packages. In certain embodiments, the cosmetic composition may include one or more optional ingredients of the kind commonly included in the particular cosmetic compositing being provided.

Dermatologically acceptable carriers should be safe for use in contact with human skin tissue. Some suitable carriers may include water and/or water miscible solvents, although other carriers may be used as known in the art. The cosmetic skin care composition may comprise from 1% to 95% by weight of water and/or water miscible solvent. In certain embodiments, the personal care composition may include water, diols, glycerin, and combinations thereof. When the skin care composition is in the form of an emulsion, water and/or water miscible solvents are carriers typically associated with the aqueous phase.

In some embodiments, the compositions herein may include an oil carrier at an amount of from 1% to 95% by weight. Oils may be used to solubilize, disperse, or carry materials that are not suitable for water or water soluble solvents. Suitable oils include silicones, hydrocarbons, esters, amides, ethers, and mixtures thereof. Oils may be fluid at room temperature. The oils may be volatile or nonvolatile. When the skin care composition is in the form of an emulsion, oils are carriers typically associated with the oil phase.

The compositions herein may include an emulsifier. An emulsifier is particularly suitable when the composition is in the form of an emulsion or if immiscible materials are being combined. The skin care composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. Non-limiting examples of emulsifiers are disclosed in U.S. Pat. No. 3,755,560, U.S. Pat. No. 4,421,769, and McCutcheon's, *Emulsifiers and Detergents,* 2010 Annual Ed., published by M. C. Publishing Co. Other suitable emulsifiers are further described in the Personal Care Product Council's *International Cosmetic Ingredient Dictionary and Handbook,* Thirteenth Edition, 2006, under the functional category of "Surfactants—Emulsifying Agents." Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu. Emulsifiers also include emulsifying silicone elastomers.

The skin care compositions may be generally prepared by conventional methods such as known in the art of making compositions and topical compositions. Such methods may involve mixing of ingredients in or more steps to a relatively uniform state, with or without heating, cooling, application of vacuum, and the like. Emulsions may be prepared by first mixing the aqueous phase materials separately from the fatty phase materials and then combining the two phases as appropriate to yield the desired continuous phase. The composition may be provided or stored in a package or container sized to store a sufficient amount of the composition for a treatment period. The size, shape, and design of the container or package may vary widely. Certain package examples are described in U.S. Pat. Nos. D570,707; D391, 162; D516,436; D535,191; D542,660; D547,193; D547, 661; D558,591; D563,221; 2009/0017080; 2007/0205226; and 2007/0040306.

EXAMPLES

The following are non-limiting examples of various aspects of the methods and models described herein. The examples are given solely for the purpose of illustration and are not to be construed as limiting the invention, as many variations thereof are possible.

Example 1

Ex Vivo Tissue Preparation

Materials for preparation included: Dulbecco's Modified Eagle Medium plus Glutamax, antibiotic and antimycotics, 1× phosphate buffer solution (PBS(-ca, -mg), 150 mm×15 mm sterile culture dishes, sterile gauze 4×4, disposable safety scalpels, 4 mm disposable biopsy punch, 6-well cell culture inserts, disinfected tweezers, cotton-tipped applicators, 6-well culture plates, ruled, disinfected cutting mat, optionally with a 12×12 ruler, scraper handle, tissue freezing medium, biopsy cassettes, frozen tissue freezing vessels, 10% formalin, shipping containers for fixed tissue, and biohazard/sharps containers.

Skin preparation involved preparation of media in advance of the arrival of skin (3× media including 500 ml DMEM plus 15 ml of antibiotic and antimycotics; the 3× referred to 3-fold levels of antibiotics/antimycotics used for the initial hour of incubation; 1× Media: 500 ml DMEM plus 5 ml of antibiotic and antimycotics). The skin arrived with the dermis (fat) side down on sterile DMEM soaked gauze in a sterile culture dish. The culture dish was taped shut and in a biohazard zip-lock baggie on an ice pack in a secondary container.

On arrival, the skin was removed from the bag and soaked in 3×DMEM media and stored at 4° C. for 1 hour. After 1 hour, the skin was removed from the 3×DMEM and rinsed with sterile 1×PBS. The skin was placed in a clean culture dish containing gauze soaked with 1×DMEM. The sample was put in culture the same day as arrival; though the sample may be stored overnight at 4° C. if desired.

In preparation for culture, the following were performed on the skin tissue. On a cutting mat, the skin tissue was positioned such that the epidermis was down and the fat was exposed. The fat was removed with a disposable scalpel by carefully grasping one corner of the skin with sterile serrated forceps and scraping the fat away with the blade held at a 45 degree angle to the skin. After the fat was removed, the surgical edges were cut off with a scalpel using a scraper as a straight edge guide and to hold the skin in place. Using the scraper as a guide, the skin was cut into 1.25 cm wide strips using a ruler (such as the one on optionally provided on the cutting mat) to measure the width. The strip was rinsed in a 100 mm culture dish containing 1×PBS. The strips were cut into 1.25 cm squares and placed in a 100 mm culture dish onto 1×DMEM soaked gauze until they were put into culture 30 minutes later (with time points of 15 minutes, 30 minutes, 45 minutes, or an hour being used in various non-limiting examples).

Example 2

Ex Vivo Tissue Culturing

Culturing involved putting 2.5 ml of media or treatment into each well of a 6-well tissue plate, adding one Millicell® brand culture insert to each well, and putting 100 μl of 1×DMEM on the center of each insert membrane. The skin sample squares were selected randomly and placed into each of the inserts (one skin sample per insert), on top of the media on the membrane. The plates were stored at 33° C. (though an additional non-limiting example would be 37° C. depending on the experiment endpoint). As a control, baseline tissue measurements were collected from excess waste (cryogenics were used for snap freezing). Baseline biopsy collection involved from each tissue piece; one 4 mm punch for MTT; one 4 mm punch (snap frozen in OCT) for fresh histology; One 4 mm punch was fixed in 10% formalin for paraffin embedding and two 4 mm punches (snap frozen in liquid nitrogen) for PCR.

Culture and treatment of the model comprised replicates of n=6 (though replicates of additional quantities may be used such as n=5). Media dosing of skin involved solubilizing compounds used in appropriate solvents (including PBS, Media, alcohol, and DMSO; in using DMSO, the final concentration in the plate was restricted to 0.01%). Appropriate dilutions were made for treatment: 15 ml of media were required per plate per day for treatment, with 2.5 ml of media required per well under the cell culture insert. Media was pre-warmed and changed every day during the experiment. The media was aspirated and replaced with fresh warmed media at a level of 2.5 ml per well. Tissue was dosed daily with DMEM control, vehicle only, and individual solubilized treatment legs.

Prior to starting experiment takedown, all tubes and plates were properly labeled. A cutting mat, forceps, 4 mm punches, a liquid nitrogen bucket, and an MTT plate setup were made available. Also, one set of tubes were acquired to obtain RNA (with in specific embodiments 6 baseline samples collected). The MTT plate was pre-labeled and 600 ul of 1 mg/ml MTT in DMEM media was added to each well. All samples were 4 mm biopsies. Using a biopsy punch (such as a Sklar 4 mm biopsy punch) and a hammer on a craft cutting mat (previously cleaned with alcohol) 2 punches for RNA were taken as well as 1 punch for MTT. The hammer was lightly tapped to take the biopsy, working with one treatment group (such as n=5 or n=6) on a mat at a time to take all necessary punches. Two punches were placed in a screw cap tube and snap frozen in liquid nitrogen. One punch was placed per well in an MTT plate. Work was performed quickly; time per treatment group to collect all samples was 5 minutes (with 5-10 minutes being non-limiting examples of time for collection). Once all groups were processed, the MTT plate was placed in an incubator for 24 hrs.

The MTT assessment involved 24 hours of incubation in an incubator. Well plates (2 ml deep) were provided with 1 ml of isoropanol per sample. One sample was placed per well, and the well was sealed and labeled. The plates were placed in 4 C for 3 days of extraction.

The MTT plate was read in the following manner: a 96 well clear flat bottom plate was used (though any cell culture plate can conceivably be used). Isopropanol was mixed in the deep well plate, after which 150 ul of each sample was pipetted into the new 96 well plate. An EPOCH plate reader with GENS software was used, and an absorbance endpoint was chosen for use (at 562 in one example).

Example 3 mRNA Processing, Nanodrop-Quantification and Purity Assessment, RNA Quantification Gel Protocol, cDNA Synthesis and PCR Setup For cryopreparation and extraction the following equipment was obtained and prepared: 2 ml round bottom tubes were prepared with 1 ml of TRIZOL as was a 5 mm stainless steel bead for each sample; a dry ice bucket was obtained and liquid nitrogen was placed in the bucket. Biopsy punches were maintained on dry ice, and samples remained frozen. Cryobags and covaris cryoprep were used in freeze fracturing of samples. To freeze fracture the samples, biopsies were placed in a cryo bag (2 per sample) and dipped in liquid nitrogen, then placed in cryoprep (setting 4). The sample bag was taken out and dipped back into nitrogen. A flattened disk was removed and placed into corresponding 2 ml tubes with TRIZOL. The disk was kept frozen in the TRIZOL. The tube was closed and snap frozen, and the whole tube was placed in liquid nitrogen. After repeating the process with all the samples, samples were placed into boxes and stored at −80 until the next step.

Before thawing the samples, a PLG Heavy Tube was prepared (Pre-Spun at 12000 rpm for 2 min) prepared (working with 24 samples at a time). Frozen round bottom tubes containing samples were thawed. The samples were bead-beat for 3-minutes at 3000 rpm. Samples were centrifuged for 10-minutes at 12000 rpm. During this time tubes were set up containing 200 ul chloroform in 1.5 ml tubes. The TRIZOL supernatant was taken and added to a chloroform tube, then vortexed (15 seconds). A total of 1.2 ml was added of Supernatant and chloroform to the PLG Tube. Samples were centrifuged for 10-minutes at 12000 rpm. The aqueous phase was removed from the PLG tube to 2 ml deep wells, and each set of 24 was collected in the same plate for storing at 4 degrees between additions (in various embodiments the plate can be frozen if the sample is not placed on the Magmax the same day).

Next, a Magmax magnetic bead RNA extraction was performed. Deepwell plate containing aqueous phase were thawed. A check was made of the wash buffers to ensure that the buffers had the appropriate alcohol amount added to the bottle. A modified wash 1 was used in order to obtain micro RNA extraction (12 ml in bottle plus 12 ml Isopropyl Alcohol). A second wash was also performed. Elution buffer was pre-made and did not need any additions.

Once plates were setup for the Magmax, the machine was turned on, the appropriate protocol was selected, and the plates were loaded. A 35 minute run cycle was performed and the plates were removed. The extraction was a heated step and extra time on the extraction plate would degrade RNA. The elution plate was sealed with foil and a lid was placed over the foil. RNA was stored at −80 until needed.

RNA Quantification Gel Protocol

An RNA quantification gel was performed, using Agilent Chip RNA-Nano. Reagents were prepared; the following Agilent reagents were removed from the 4 C fridge: Agilent Blue (Dye), Agilent Yellow (Nano ladder, before use heated for 2 min at 70°, placed on ice, aliquoted in 5 ul into tubes and stored in −20 C), Agilent Green, and Agilent Red (gel). Reagents were allowed to warm up to room temperature for 10 minutes. Pipetting of 550 µl Agilent Red (Gel) was performed into a filter column and centrifuged for 10 minutes at 1500 g at room temperature. Agilent Blue (Dye) was vortexed for 10 seconds. 65 µl of filtered gel was aliquotted into a tube, 1 µl of Agilent Blue (Dye) was added, and the tube was centrifuged at 13000 g for 10 minutes. Next an Agilent chip was loaded into the priming station along with 9 µl of Gel-Dye Mix. The priming station was closed for 30 seconds and the plunger was subsequently pulled. The priming station was loaded with 9 µl of Gel-Dye mix into the remaining 2 G-Wells. Regarding loading of the ladder samples, the following was used: Pipetting of 5 µl of Agilent Green into each of the wells being used, including the ladder well (in unused wells, 6 µl was added of Agilent Green), 1 µl of Agilent Yellow (Nano Ladder) was added into the Ladder Well, 1 µl of sample was added into each well; vortexing in a chip shaker was performed for 1 minute, upon which an Agilent Analyzer was used.

cDNA Synthesis

From the mRNA samples, cDNA was synthesized. cDNA reactions were made in a 0.2 ml PCR strip tube with mastermix first then sample volume and finally water. Lids were closed, and mixing and spin-downs were performed. Tubes were placed in a thermal cycler, a run was performed, and samples were held at 4 degrees; then subsequently stored at −20 until need for a PCR reaction.

PCR Setup

PCR was performed using Quanta Perfecta Sybr green master mix with ROX. PCR plates were number coded for the project. All plates came pre-plated with the primers needed for PCR. Reagents were mixed, then the reaction mixture was aliquoted across the plates putting 20 ul per well. Plate setup was 12×8, 8 samples down the plate and 12 genes across. Setup reactions were in 0.5 ml tubes. PCR plates were at room temperature before use. Mastermix was centrifuged before use. PCR analysis involved StepOne software and use of housekeeping genes and geometric means.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A screening method for identifying an agent as effective for providing an anti-aging skin benefit, comprising:
   a. culturing first and second human skin samples for about 3 days to about 19 days, wherein the first and second human skin samples each comprise an epidermal layer and a dermal layer and are obtained from human donor tissue;
   b. contacting the first human skin sample with at least one test agent;
   c. contacting the second human skin sample with a positive control;
   d. generating a transcriptional profile from the first and second human skin samples of a set of genes consisting of fibrillin 1 (FBN1), fibulin 1 (FBLN1), tenascin XB (TNXB), fibronectin 1 (FN1), lysyl oxidase homolog 2 (LOXL2), collagen, type I, alpha 1 (COL1A1), collagen, type III, alpha 1 (COL3A1), elastin (ELN), and lysyl oxidase-like 1 (LOXL1);
   e. determining a change in the direction of regulation of FBN1, FBLN1, TNXB, FN1, LOXL2, COL1A1, COL3A1, ELN, and LOXL1 for the first and second human skin samples based on the transcriptional profiles of (d); and
   f. identifying the test agent as effective for providing an anti-aging skin benefit when the change in direction of regulation of the genes in (e) is the same for the first and second skin samples.

2. The screening method of claim 1, wherein contacting the at least one test agent is by addition of the at least one test agent to a culture medium.

3. The screening method of claim 1, wherein the positive control is selected from the group consisting of a vitamin B3 compound, a peptide, a vitamin A compound, a transforming growth factor (TGF) and combinations thereof.

4. The screening method of claim 1, further comprising repeating steps a) to d), wherein the first and second human skin samples for each repetition are obtained from donor tissue from different human donors.

5. The screening method of claim 4, wherein the at least one test agent is different for each repetition.

6. The screening method of claim 1, further comprising testing the at least one test agent in an enzyme assay, a cell culture assay, or a skin equivalent assay.

7. The screening method of claim 1, wherein the first and second human skin samples are cultured at a relative humidity from about 50% to about 90% and a temperature from about 30° C. to about 40° C.

8. The screening method of claim 1, wherein at least one of the first and second human skin samples is cultured on a membrane.

9. A screening method for identifying a combination of agents as effective for providing an anti-aging skin benefit, comprising:
   a. culturing a first human skin sample and a plurality of second human skin samples from about 3 days to about 19 days, wherein the first human skin sample and the plurality of second human skin samples each comprise an epidermal layer and a dermal layer and are obtained from human donor tissue;
   b. contacting the first human skin sample with a combination of two or more test agents;
   c. contacting each of the plurality of second human skin samples with one of the test agents;
   d. generating transcriptional profiles from the first human skin sample and the plurality of second human skin samples, of a set of genes consisting of FBN1, FBLN1, TNXB, FN1, LOXL2, COL1A1, COL3A1, ELN, and LOXL1;
   e. determining a change in the direction of regulation of FBN1, FBLN1, TNXB, FN1, LOXL2, COL1A1, COL3A1, ELN, and LOXL1 for the first human skin sample and the plurality of second human skin samples from the transcriptional profiles of (d); and
   f. identifying the combination of test agents as effective for providing an anti-aging skin benefit when the change in direction of regulation of the genes in (d) for the first human skin samples shows a synergistic response compared to the change in direction of regulation of the genes in (d) for the plurality of second human skin samples.

10. The screening method of claim 9, wherein the synergistic response comprises the transcriptional profiles of the genes from the plurality of second human skin samples being regulated in a first direction and the transcriptional profiles of the genes selected from the first human skin sample being regulated in an opposite direction.

11. The screening method of claim 9, wherein the synergistic response comprises the transcriptional profiles of the genes from the first human skin sample being more than or less than the addition of the transcriptional profiles of the genes from the plurality of second human skin samples.

* * * * *